(12) United States Patent
Choi et al.

(10) Patent No.: US 7,902,346 B2
(45) Date of Patent: Mar. 8, 2011

(54) FUSION PROTEIN COMPRISING FK506 BINDING PROTEIN AND DNA ENCODING THE SAME

(75) Inventors: Soo Young Choi, Gangwon-do (KR); Jinseu Park, Gangwon-do (KR); Won Sik Eum, Gangwon-do (KR); Dae-Won Kim, Osan-si (KR); Jin-Hee Choi, Gangwon-do (KR); Tae-Yoon Kim, Seoul (KR); Hyung-Joo Kwon, Cheongju-si (KR)

(73) Assignee: Industry Academic Cooperation Foundation, Hallym University, Chuncheon, Gangwon-do (KR)

( * ) Notice: Subject to any disclaimer, the term of this patent is extended or adjusted under 35 U.S.C. 154(b) by 0 days.

(21) Appl. No.: 12/144,890

(22) Filed: Jun. 24, 2008

(65) Prior Publication Data
US 2008/0280830 A1 Nov. 13, 2008

Related U.S. Application Data

(63) Continuation of application No. PCT/KR2007/001144, filed on Mar. 8, 2007.

(30) Foreign Application Priority Data

Mar. 23, 2006 (KR) .......... 10-2006-0026318

(51) Int. Cl.
*C07H 21/04* (2006.01)
*C07K 14/00* (2006.01)
*C12P 21/00* (2006.01)

(52) U.S. Cl. .......... 536/23.1; 536/23.4; 530/350
(58) Field of Classification Search .......... None
See application file for complete search history.

(56) References Cited

U.S. PATENT DOCUMENTS
6,387,700 B1    5/2002    Rice et al.

FOREIGN PATENT DOCUMENTS
| KR | 2004/0075236 A | 8/2004 |
| KR | 2005/0005659 A | 1/2005 |
| KR | 2006/0017348 A | 2/2006 |
| WO | WO 97/38011 A1 | 10/1997 |

OTHER PUBLICATIONS

Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Wang et al. The immunophilin FKBP12: a molecular guardian of the TGF-beta family type I receptors. Frontiers in Biosci 9: 619-631, 2004.*
Woo et al. Topical tacrolimus: a review of its uses in dermatology. Dermatitis 16(1): 6-21, 2005.*
Magzoub et al. Cell-penetrating peptides: small from inception to application. Quart Rev Biophys 37(2): 147-195, 2004.*
Chow et al. The use of tacrolimus in the treatment of inflammatory bowel disease. Expert Opin Drug Saf 6(5): 479-485, 2007.*
Kang et al. FKBP family proteins: immunophilins with versatile biological functions. Neurosignals 16: 318-325, 2008.*
Barik et al. Immunophilins: for the love of proteins. Cell Mol Life Sci 63: 2889-2900, 2006.*
Jarver et al. The use of cell-penetrating peptides as a tool for gene regulation. Drug Disc Today 9(9): 395-402, 2004.*
Fong et al. Functional identification of distinct sets of antitumor activities mediated by the FKBP gene family. Proc Natl Acad Sci USA 100(24): 14253-14258 and supplemental pp. 1-3, 2003.*
Bang et al., "Activation of $Ca^{2+}$ signaling in neurotrophils by the mast cell-released immunophilin FKBP12", *Proc. Natl. Acad. Sci. USA*, 92: 3435-3438. (1995).
Boguniewicz et al., "Atopic dermatitis", *J. Allergy Clin. Immunol.* 117(2): S475-S480. (2006).
Bornhövd et al., "Macrolactam immunomodulators for topical treatment of inflammatory skin diseases", *J. Am. Acad. Dermatol.* 45(5): 736-743. (2001).
Bradford, M.M., "A rapid and sensitive method for the quantitation of microgram quantities of protein utilizing the principle of protein-dye binding", *Anal. Biochem.* 72: 248-254. (1976).
Breuer et al., "Topical immunomodulators in the treatment of atopic dermatitis", *J. Lab. Med.* 28(3): 284-287 (2004).
Castro, A.P.B.M. "Calcineurin inhibitors in the treatment of allergic dermatitis", *J. Pediatr. (Rio J)* 82(5 Suppl): S166-S172. (2006).
Del Zoppo et al., "Trends and future developments in the pharmacological treatment of acute ischaemic stroke", *Drugs*, 54(1): 9-38. (1997).
Fruman et al., "The complex of FK506-binding protein 12 and FK506 inhibits calcineurin phosphatase activity and IgE activation-induced cytokine transcripts, but not exocytosis, in mouse mast cells", *J. Immunol.* 154: 1846-1851. (1995).
Leung et al., "Atopic dermatitis", *The Lancet*, 361: 151-160. (2003).
Leung, D.Y.M., "Atopic dermatitis: New insights and opportunities for therapeutic intervention", *J. Allergy Clin. Immunol.* 105: 860-876. (2000).

(Continued)

*Primary Examiner* — Bridget E Bunner
(74) *Attorney, Agent, or Firm* — Knobbe Martens Olson & Bear LLP (57) ABSTRACT

Disclosed is a fusion protein containing a FK506 binding protein and a cell-transducing domain. Also, disclosed is a method of making the fusion protein and use of the fusion protein in a pharmaceutical or cosmetic composition. The cell-transducing domain is, for example, a PEP-1.

3 Claims, 3 Drawing Sheets

OTHER PUBLICATIONS

Matsuda et al., "Regulation of MAPK signaling pathways through immunophilin-ligand complex", *Curr. Top. Med. Chem.* 3: 1358-1367. (2003).

Morris et al., "A peptide carrier for the delivery of biologically active proteins into mammalian cells", *Nat. Biotech.* 19: 1173-1176. (2001).

Novak et al., "Immune mechanisms leading to atopic dermatitis", *J. Allergy Clin. Immunol.* 112(6): S128-S139. (2003).

Panhans-Groβ et al., "Human epidermal Langerhans' cells are targets for the immunosuppressive macrolide tacrolimus (FK506)", *J. Allergy Clin. Immunol.* 107: 345-352. (2001).

Reitamo, S., "Tacrolimus: A new topical immunomodulatory therapy fro atopic dermatitis", *J. Allergy Clin. Immunol.* 107: 445-448. (2001).

Sambrook et al., "Molecular cloning: Preparation of Plasmid DNA . . . ", *Cold spring harbor laboratory press*, Cold spring harbor. pp. 1.32-1.42. (1989).

DeCenzo, Maureen et al., "FK506-binding protein mutational analysis: defining the active-site residue contributions to catalysis and the stability of ligand complexes," Protein Engineering, 1996, vol. 9, No. 2, pp. 173-180.

Fulton, Kate F. et al., "Energetic and structural analysis of the role of tryptophan 59 in FKBP12," Biochemistry, 2003, vol. 42, No. 8, pp. 2364-2372.

Futer, Olga et al., "FK506 binding protein mutational analysis," The Journal of Biological Chemistry, Aug. 11, 1995, vol. 270, No. 32, pp. 18935-18940.

Gros, Edwige et al., "A non-covalent peptide-based strategy for protein and peptide nucleic acid transduction," Biochimica et Biophysica Acta, 2006, vol. 1758, pp. 384-393.

Henriques, Sonia T. et al., "Re-evaluating the role of strongly charged sequences in amphipathic cell-penetrating petides; a fluorescence study using pep-1," FEBS Letters, 2005, vol. 579, pp. 4498-4502.

Parsons, Janey N. et al., "Regulation of calcineurin phosphatase activity and interaction with the FK-506•FK-506 binding protein complex," The Journal of Biological Chemistry, Jul. 29, 1994, vol. 269, No. 30, pp. 19610-19616.

Weller, K. et al., "Biophysical and biological studies of end-group-modified derivatives pep-1," Biochemistry, 2005, vol. 44, No. 48, pp. 15799-15811.

* cited by examiner

← 18 KDa

C   1   3   6   12   24   36   48   60   (hours)

Figure 5

COX-2

| PEP-1-FKBP | 0 | 0 | 0 | 10 | 10 | (μM) |
| FK506 | - | - | + | - | + | (1 μg/ml) |
| LPS | - | + | + | + | + | (100 ng/ml) |

Figure 6

1) control

2) PEP-1-FK506BP

3) FK506BP-PEP-1

4) PEP-1-FK506BP-PEP-1

SEQUENCE LISTING

<160> NUMBER OF SEQ ID NOS: 11

<210> SEQ ID NO 1
<211> LENGTH: 68
<212> TYPE: DNA
<213> ORGANISM: Artificial Sequence
<220> FEATURE:
<223> OTHER INFORMATION: top strand oligonucleotide coding PEP-1

<400> SEQUENCE: 1
tatgaaagaa acctggtggg aaacctggtg gaccgaatgg tctcagccga aaaaaaacg      60 taaagtgc                                                             68

<210> SEQ ID NO 2
<211> LENGTH: 70
<212> TYPE: DNA

<213> ORGANISM: Artificial Sequence
<220> FEATURE:
<223> OTHER INFORMATION: bottom strand oligonucleotide coding PEP-1

<400> SEQUENCE: 2
tcgagcactt tacgttttt tttcggctga caccattcgg tccaccaggt ttcccaccag    60
gtttctttcc                                                          70

<210> SEQ ID NO 3
<211> LENGTH: 21
<212> TYPE: PRT
<213> ORGANISM: Artificial Sequence
<220> FEATURE:
<223> OTHER INFORMATION: protein transducing domain called PEP-1

<400> SEQUENCE: 3

Lys Glu Thr Trp Trp Glu Thr Trp Trp Thr Glu Trp Ser Gln Pro Lys
 1               5                  10                  15

Lys Lys Arg Lys Val
            20

<210> SEQ ID NO 4
<211> LENGTH: 30
<212> TYPE: DNA
<213> ORGANISM: Artificial Sequence
<220> FEATURE:
<223> OTHER INFORMATION: forward primer of human FK506binding protein

<400> SEQUENCE: 4
ctcgagatgg gagtgcaggt ggaaaccatc                                    30

<210> SEQ ID NO 5
<211> LENGTH: 30
<212> TYPE: DNA
<213> ORGANISM: Artificial Sequence
<220> FEATURE:
<223> OTHER INFORMATION: reverse primer of human FK506 binding protein

<400> SEQUENCE: 5
ggatcctcat tccagtttta gaagctccac                                    30

<210> SEQ ID NO 6
<211> LENGTH: 402
<212> TYPE: DNA
<213> ORGANISM: Artificial Sequence
<220> FEATURE:
<223> OTHER INFORMATION: recombinant polynucleotide coding PEP-1-FK506
      binding protein fusion protein
<220> FEATURE:
<221> NAME/KEY: CDS
<222> LOCATION: (1)..(393)

<400> SEQUENCE: 6 atg aaa gaa acc tgg tgg gaa acc tgg tgg acc gaa tct cag ccg aaa    48
Met Lys Glu Thr Trp Trp Glu Thr Trp Trp Thr Glu Ser Gln Pro Lys
 1               5                  10                  15 aaa aaa cgt aaa gtg ctc gag atg gga gtg cag gtg gaa acc atc tcc    96
Lys Lys Arg Lys Val Leu Glu Met Gly Val Gln Val Glu Thr Ile Ser
            20                  25                  30 cca gga gac ggg cgc acc ttc ccc aag cgc ggc cag acc tgc gtg gtg   144
Pro Gly Asp Gly Arg Thr Phe Pro Lys Arg Gly Gln Thr Cys Val Val
        35                  40                  45 cac tac acc ggg atg ctt gaa gat gga aag aaa ttt gat tcc tcc cgg   192
His Tyr Thr Gly Met Leu Glu Asp Gly Lys Lys Phe Asp Ser Ser Arg
    50                  55                  60

```
gac aga aac aag ccc ttt aag ttt atg cta ggc aag cag gag gtg atc         240
Asp Arg Asn Lys Pro Phe Lys Phe Met Leu Gly Lys Gln Glu Val Ile
65                  70                  75                  80 cga ggc tgg gaa gaa ggg gtt gcc cag atg agt gtg ggt cag aga gcc         288
Arg Gly Trp Glu Glu Gly Val Ala Gln Met Ser Val Gly Gln Arg Ala
                85                  90                  95 aaa ctg act ata tct cca gat tat gcc tat ggt gcc act ggg cac cca         336
Lys Leu Thr Ile Ser Pro Asp Tyr Ala Tyr Gly Ala Thr Gly His Pro
            100                 105                 110 ggc atc atc cca cca cat gcc act ctc gtc ttc gat gtg gag ctt cta         384
Gly Ile Ile Pro Pro His Ala Thr Leu Val Phe Asp Val Glu Leu Leu
        115                 120                 125 aaa ctg gaa    tgaggat cc                                               402
Lys Leu Glu
    130

<210> SEQ ID NO 7
<211> LENGTH: 131
<212> TYPE: PRT
<213> ORGANISM: Artificial Sequence
<220> FEATURE:
<223> OTHER INFORMATION: PEP-1-FK506 binding protein fusion protein

<400> SEQUENCE: 7

Met Lys Glu Thr Trp Trp Glu Thr Trp Trp Thr Glu Ser Gln Pro Lys
1               5                   10                  15

Lys Lys Arg Lys Val Leu Glu Met Gly Val Gln Val Glu Thr Ile Ser
                20                  25                  30

Pro Gly Asp Gly Arg Thr Phe Pro Lys Arg Gly Gln Thr Cys Val Val
            35                  40                  45

His Tyr Thr Gly Met Leu Glu Asp Gly Lys Lys Phe Asp Ser Ser Arg
        50                  55                  60

Asp Arg Asn Lys Pro Phe Lys Phe Met Leu Gly Lys Gln Glu Val Ile
65                  70                  75                  80

Arg Gly Trp Glu Glu Gly Val Ala Gln Met Ser Val Gly Gln Arg Ala
                85                  90                  95

Lys Leu Thr Ile Ser Pro Asp Tyr Ala Tyr Gly Ala Thr Gly His Pro
            100                 105                 110

Gly Ile Ile Pro Pro His Ala Thr Leu Val Phe Asp Val Glu Leu Leu
        115                 120                 125

Lys Leu Glu
    130

<210> SEQ ID NO 8
<211> LENGTH: 402
<212> TYPE: DNA
<213> ORGANISM: Artificial Sequence
<220> FEATURE:
<223> OTHER INFORMATION: recombinant polynucleotide coding FK506
      binding protein-PEP-1 fusion protein
<220> FEATURE:
<221> NAME/KEY: CDS
<222> LOCATION: (1)..(399)

<400> SEQUENCE: 8 ctc gag atg gga gtg cag gtg gaa acc atc tcc cca gga gac ggg cgc         48
Leu Glu Met Gly Val Gln Val Glu Thr Ile Ser Pro Gly Asp Gly Arg
1               5                   10                  15 acc ttc ccc aag cgc ggc cag acc tgc gtg gtg cac tac acc ggg atg         96
Thr Phe Pro Lys Arg Gly Gln Thr Cys Val Val His Tyr Thr Gly Met
                20                  25                  30 ctt gaa gat gga aag aaa ttt gat tcc tcc cgg gac aga aac aag ccc         144
```

```
                                                        -continued

Leu Glu Asp Gly Lys Lys Phe Asp Ser Ser Arg Asp Arg Asn Lys Pro
         35                  40                  45 ttt aag ttt atg cta ggc aag cag gag gtg atc cga ggc tgg gaa gaa      192
Phe Lys Phe Met Leu Gly Lys Gln Glu Val Ile Arg Gly Trp Glu Glu
     50                  55                  60 ggg gtt gcc cag atg agt gtg ggt cag aga gcc aaa ctg act ata tct      240
Gly Val Ala Gln Met Ser Val Gly Gln Arg Ala Lys Leu Thr Ile Ser
 65                  70                  75                  80 cca gat tat gcc tat ggt gcc act ggg cac cca ggc atc atc cca cca      288
Pro Asp Tyr Ala Tyr Gly Ala Thr Gly His Pro Gly Ile Ile Pro Pro
                 85                  90                  95 cat gcc act ctc gtc ttc gat gtg gag ctt cta aaa ctg gaa gga tcc      336
His Ala Thr Leu Val Phe Asp Val Glu Leu Leu Lys Leu Glu Gly Ser
            100                 105                 110 atg aaa gaa acc tgg tgg gaa acc tgg tgg acc gaa tct cag ccg aaa      384
Met Lys Glu Thr Trp Trp Glu Thr Trp Trp Thr Glu Ser Gln Pro Lys
        115                 120                 125 aaa aaa cgt aaa gtg t ag                                             402
Lys Lys Arg Lys Val
        130

<210> SEQ ID NO 9
<211> LENGTH: 133
<212> TYPE: PRT
<213> ORGANISM: Artificial Sequence
<220> FEATURE:
<223> OTHER INFORMATION: FK506 binding protein-PEP-1 fusion protein

<400> SEQUENCE: 9

Leu Glu Met Gly Val Gln Val Glu Thr Ile Ser Pro Gly Asp Gly Arg
 1               5                  10                  15

Thr Phe Pro Lys Arg Gly Gln Thr Cys Val Val His Tyr Thr Gly Met
             20                  25                  30

Leu Glu Asp Gly Lys Lys Phe Asp Ser Ser Arg Asp Arg Asn Lys Pro
         35                  40                  45

Phe Lys Phe Met Leu Gly Lys Gln Glu Val Ile Arg Gly Trp Glu Glu
     50                  55                  60

Gly Val Ala Gln Met Ser Val Gly Gln Arg Ala Lys Leu Thr Ile Ser
 65                  70                  75                  80

Pro Asp Tyr Ala Tyr Gly Ala Thr Gly His Pro Gly Ile Ile Pro Pro
                 85                  90                  95

His Ala Thr Leu Val Phe Asp Val Glu Leu Leu Lys Leu Glu Gly Ser
            100                 105                 110

Met Lys Glu Thr Trp Trp Glu Thr Trp Trp Thr Glu Ser Gln Pro Lys
        115                 120                 125

Lys Lys Arg Lys Val
        130

<210> SEQ ID NO 10
<211> LENGTH: 465
<212> TYPE: DNA
<213> ORGANISM: Artificial Sequence
<220> FEATURE:
<223> OTHER INFORMATION: recombinant polynucleotide coding PEP-1-FK506
      binding protein-PEP-1 fusion protein
<220> FEATURE:
<221> NAME/KEY: CDS
<222> LOCATION: (1)..(462)

<400> SEQUENCE: 10 atg aaa gaa acc tgg tgg gaa acc tgg tgg acc gaa tct cag ccg aaa       48
Met Lys Glu Thr Trp Trp Glu Thr Trp Trp Thr Glu Ser Gln Pro Lys
```

```
                1               5              10              15
aaa aaa cgt aaa gtg ctc gag atg gga gtg cag gtg gaa acc atc tcc        96
Lys Lys Arg Lys Val Leu Glu Met Gly Val Gln Val Glu Thr Ile Ser
                20              25              30 cca gga gac ggg cgc acc ttc ccc aag cgc ggc cag acc tgc gtg gtg       144
Pro Gly Asp Gly Arg Thr Phe Pro Lys Arg Gly Gln Thr Cys Val Val
        35              40              45 cac tac acc ggg atg ctt gaa gat gga aag aaa ttt gat tcc tcc cgg       192
His Tyr Thr Gly Met Leu Glu Asp Gly Lys Lys Phe Asp Ser Ser Arg
 50              55              60 gac aga aac aag ccc ttt aag ttt atg cta ggc aag cag gag gtg atc       240
Asp Arg Asn Lys Pro Phe Lys Phe Met Leu Gly Lys Gln Glu Val Ile
 65              70              75              80 cga ggc tgg gaa gaa ggg gtt gcc cag atg agt gtg ggt cag aga gcc       288
Arg Gly Trp Glu Glu Gly Val Ala Gln Met Ser Val Gly Gln Arg Ala
                85              90              95 aaa ctg act ata tct cca gat tat gcc tat ggt gcc act ggg cac cca       336
Lys Leu Thr Ile Ser Pro Asp Tyr Ala Tyr Gly Ala Thr Gly His Pro
        100             105             110 ggc atc atc cca cca cat gcc act ctc gtc ttc gat gtg gag ctt cta       384
Gly Ile Ile Pro Pro His Ala Thr Leu Val Phe Asp Val Glu Leu Leu
 115             120             125 aaa ctg gaa gga tcc atg aaa gaa acc tgg tgg gaa acc tgg tgg acc       432
Lys Leu Glu Gly Ser Met Lys Glu Thr Trp Trp Glu Thr Trp Trp Thr
130             135             140 gaa tct cag ccg aaa aaa aaa cgt aaa gtg          tag                  465
Glu Ser Gln Pro Lys Lys Lys Arg Lys Val
145             150

<210> SEQ ID NO 11
<211> LENGTH: 154
<212> TYPE: PRT
<213> ORGANISM: Artificial Sequence
<220> FEATURE:
<223> OTHER INFORMATION: PEP-1-FK506 binding protein-PEP-1 fusion
      protein

<400> SEQUENCE: 11

Met Lys Glu Thr Trp Trp Glu Thr Trp Trp Thr Glu Ser Gln Pro Lys
 1               5              10              15

Lys Lys Arg Lys Val Leu Glu Met Gly Val Gln Val Glu Thr Ile Ser
                20              25              30

Pro Gly Asp Gly Arg Thr Phe Pro Lys Arg Gly Gln Thr Cys Val Val
        35              40              45

His Tyr Thr Gly Met Leu Glu Asp Gly Lys Lys Phe Asp Ser Ser Arg
 50              55              60

Asp Arg Asn Lys Pro Phe Lys Phe Met Leu Gly Lys Gln Glu Val Ile
 65              70              75              80

Arg Gly Trp Glu Glu Gly Val Ala Gln Met Ser Val Gly Gln Arg Ala
                85              90              95

Lys Leu Thr Ile Ser Pro Asp Tyr Ala Tyr Gly Ala Thr Gly His Pro
        100             105             110

Gly Ile Ile Pro Pro His Ala Thr Leu Val Phe Asp Val Glu Leu Leu
 115             120             125

Lys Leu Glu Gly Ser Met Lys Glu Thr Trp Trp Glu Thr Trp Trp Thr
130             135             140

Glu Ser Gln Pro Lys Lys Lys Arg Lys Val
145             150
```

FUSION PROTEIN COMPRISING FK506 BINDING PROTEIN AND DNA ENCODING THE SAME

CROSS-REFERENCE TO RELATED PATENT APPLICATIONS

This application is a continuation application under 35 U.S.C. §365(c) of International Application No. PCT/KR2007/001144, filed Mar. 8, 2007 designating the United States. The International Application No. PCT/KR2007/001144 was published in English as WO2007/108595 A1 on Sep. 27, 2007. This application further claims the benefit of the earlier filing date under 35 U.S.C. §365(b) of Korean Patent Application No. 10-2006-0026318 filed Mar. 23, 2006. This application incorporates herein by reference the International Application No. PCT/KR2007/001144 including the International Publication No. WO2007/108595 A1 and the Korean Patent Application No. 10-2006-0026318 in their entirety.

BACKGROUND

The present disclosure relates to a cell-transducing fusion protein. More specifically, the fusion protein contains a FK506 binding protein, a portion thereof or an analog thereof. Further, the present disclosure relates to method of making the fusion protein, method of using and compositions containing the fusion protein.

SUMMARY

One aspect of the invention provides a fusion protein, which comprises: an FK506 binding protein moiety; and at least one transducing moiety binding with the FK506 binding protein, wherein the at least one transducing moiety comprises a hydrophobic domain and a hydrophilic domain.

In the fusion protein, the FK 506 binding protein moiety may comprise an amino terminal and a carboxyl terminal, wherein the at least one transducing moiety is bonded to at least one of the amino terminal and carboxyl terminal. Further, the hydrophobic domain may comprise at least 5 tryptophans. The hydrophilic domain may comprise at least 4 lysines. The at least one transducing moiety may comprise a Pep-1 peptide. The at least one transducing moiety may comprise a sequence of SEQ ID NO: 3. The fusion protein may comprise a sequence selected from the group consisting of SEQ ID NO:7, SEQ ID NO:9, SEQ ID NO:11, and amino acid sequences having about 85% to about 100% similarity to one of the sequences of SEQ ID NO:7, SEQ ID NO:9, and SEQ ID NO:11. The FK506 binding protein moiety may comprise a human FK506 binding protein or a derivative thereof having about 85% to about 100% similarity to a human FK506 binding protein sequence.

Another aspect of the invention provides a composition comprising the foregoing fusion protein.

Another aspect of the invention provides a composition comprising a fusion protein, which comprises: an FK506 binding protein moiety, and at least one transducing moiety binding with the FK506 binding protein, wherein the at least one transducing moiety comprises a Pep-1 peptide. The foregoing composition may be a pharmaceutical composition and further may comprise a pharmaceutically acceptable carrier.

Still another aspect of the invention provides a method of treating a patient in need of a FK506 binding protein, the method comprising: administering the foregoing pharmaceutical composition. In the foregoing method, administering may comprise at least one selected from the group consisting of oral administration, injection, intravenous introduction, intrathecal application, topical application and application using a patch containing the composition. The composition may be a skin care cosmetic composition.

A further aspect of the invention provides a method of using the foregoing composition. The method comprises: applying the composition on a skin.

A still further aspect of the invention provides a recombinant polynucleotide comprising at least one DNA sequence encoding a cell-transducing moiety and a cDNA encoding an FK506 binding protein moiety. In the foregoing polynucleotide, the at least one DNA sequence may be configured to encode a Pep-1 transduction moiety. The at least one DNA sequence may be conjugated with an amino or carboxyl encoding end of the cDNA. The polynucleotide may be configured to encode a cell-transducing fusion protein comprising an FK506 binding protein moiety. The polynucleotide may be selected from the group consisting of SEQ ID NO:6, SEQ ID NO:8 and SEQ ID NO:10.

A still further aspect of the invention provides a vector expressing a cell-transducing fusion protein comprising the foregoing polynucleotide.

A fusion protein containing an FK506 binding protein was produced and tested for cell transducing, stability and biological activities. The fusion protein showed a desirable level of cell transducing effect, at least 48 hour stability within cells, and sufficient biological activities in the cells. The fusion protein can be used in treating patients in need of FK506 and in cosmetics.

DETAILED DESCRIPTION OF EMBODIMENTS

Allergy is a symptom representing hypersensitive responses of the immune metabolism in human body to certain foreign substances. Especially, one type of recently increasing allergy is atopy dermatitis, which is a chronic inflammatory dermatitis, generally started in infancy or childhood and continued to adulthood or started in adulthood.

Atopy dermatitis is characterized as pruritus and chronic recurring eczema, and lichenification, excoriation in chronic state. Sometimes atopy is accompanied with allergic rhinitis, asthma or respiratory diseases.

The causes of atopy are not completely discovered, a genetic factor, new lifestyles, environmental pollutions, use of chemical substances, use of antibiotics and another environmental factors are known to bring atopy. Recent researches have reported that over-produced interleukin 4(IL-4) as a $T_H2$ cytokine increases a concentration of IgE in serum, and abnormally low expressed interferon-γ(IFN-γ) as a $T_H1$ cytokine inhibits the function of $T_H2$ cells. So to speak, a balance of the two substances is important. But in atopy dermatitis, the balance breaks down and IgE is over-produced. This immune factor is known to be one of the factors of atopy, too.

A FK506 binding protein ("FK506BP") belongs to an immunophilin family like cyclophilin A, and an abundant cytosolic receptor protein which has peptidyl-prolyl-isomerase activity. The FK506 binding protein forms a complex with an immunosuppressive drug FK506 or rapamycin in cell membrane, and the complex regulates the expression of cytokine by participating in a signaling system for T cell activation. And, the FK506 biding protein is reported to be participated in $Ca^{2+}$ signaling system, too.

An interest in macromolecules including a FK506 binding protein for use in gene therapy has been increased. Now, the most attention-attracted method is gene therapy. But, the gene therapy seems to have many issues to overcome. First, delivering of a gene is not so easy. Second, the expression rate of a gene in target cell may be low. The expression time of the protein in target cell may be short. And, an artificial control of the amount of protein expressed in target cell may be very difficult.

In transduction of drugs or proteins for treating into cell, direct transduction passing target protein through membrane could be thought. But, a protein is very difficult to pass through membrane because of mass and other biological properties of a protein. Generally, a molecule larger than 600 dalton is known to be difficult to pass through a plasma membrane.

Recently, it has been reported to deliver a natural protein into cell by Pep-1 peptide as a protein delivering method. Pep-1 peptide consists of 21 amino acids (KETWWETWW-TEW SQP KKKRKV) (SEQ ID NO: 3), and has 3 domains (hydrophobic domain, spacer, and hydrophilic domain). It has been reported that if Pep-1 peptide and an extracellular protein were added together to cell, the protein could be transduced into cell in its native form. Pep-1 peptide has been also reported that it has many advantages as a protein therapy reagent when compared to Tat peptide in terms of transduction rate, stability in biological buffer, a reduced sensitivity against serum etc. However, it was reported Pep-1 peptide should be administered in a certain ratio with the extracellular protein such as green fluorescent protein or β-galactosidase and etc. to be transduced into cell effectively. But, until now all proteins containing treating proteins were not obviously reported to be delivered into cell by Pep-1 peptide.

According to one embodiment of the present invention, an expression vector for a Pep-1-FK506 binding protein is constructed. In the expression vector, for example, cDNA of a human FK506 binding protein, a Pep-1 peptide and 6 H is residues are arranged consecutively or sequentially. Using the vector, a fusion protein of Pep-1-FK506 binding protein was over-expressed in *E. coli* and then purified using $Ni^{2+}$-affinity chromatography. The amount of Pep-1-FK506 binding protein over-expressed was very large, and as a result, the amount of purified protein was large, too. The Pep-1-FK506 binding protein was delivered into cell in concentration-dependent and time-dependent manner by western blot analysis. The Pep-1-FK506 binding protein transduced into cells stayed at least 48 hrs, and inhibited effectively cyclooxygenase-2 induced by lipopolysaccharide.

The results mean that the Pep-1-FK506 binding protein fusion protein is easily transduced and represents the biological activity of FK506 binding protein in cell. Therefore, the fusion protein of FK506 binding protein can be used to treatment of diseases including skin diseases.

Another aspect of the invention provides a pharmaceutical composition containing the fusion protein of Pep-1-FK506 binding protein as an active ingredient. In one embodiment, the pharmaceutical composition can be formulated into a liniment or injection form together with a pharmaceutically acceptable carrier. The injection composition is preferably in the form of isotonic aqueous solution or suspension, and it is sterilized and if necessary, contains aids (preservatives, stabilizers, wetting agents, emulsifying accelerators, salts for adjusting osmotic pressure, and/or buffers). In addition, they may also contain therapeutically useful substances.

The pharmaceutical formulation thus produced can be administered by parenteral routes, including intravenous, subcutaneous, intra-abdominal or topical routes, at a dosage of 0.001 µg-10 mg/kg one to several times a day. The dosage for a certain patient can vary depending on the patient's body weight, age, sex and health, the period of time and method for administration, and the severity of diseases, etc.

Furthermore, the liniment composition can be easily produced in any form according to a conventional method. For example, in producing cream, the fusion protein of an embodiment is added to a general oil-in-water (O/W) or water-in-oil (W/O) cream base, to which perfumes, chelating agents, pigments, antioxidants, preservatives and the like are added in combination with synthetic or natural materials, such as proteins, minerals and vitamins, for the purpose of improving the physical properties of the cream.

In other embodiments, the fusion protein can be used in forming a cosmetic composition including, for example, cosmetic water, gel, water-soluble powder, oil-soluble powder, water-soluble liquid, cream, essence and the like, to which pH controlling substance, perfumes, emulsifier, antiseptic and the like may be added by a conventional method.

The present inventors identified that the Pep-1-FK506 binding protein fusion protein was effectively penetrated into epidermis of mouse. Therefore, the present inventors found out that the Pep-1-FK506 binding protein fusion protein can be used as a major ingredient of pharmaceutical compositions and/or liniment (dermal application) compositions.

One aspect of the invention provides a method of delivering a FK506 binding protein into cell or skin effectively. In one embodiment, the intracellular transduction of FK506 binding protein molecule is performed by constructing a fusion protein in which a FK506 binding protein bound to at least one transducing domain containing 15-30 amino acids, hydrophobic domain containing at least 5 tryptophans, hydrophilic domain containing at least 4 lysines, and spacer separating the said two domains. An example of the said transducing domain is Pep-1 peptide such as Seq. No. 3 comprising 21 amino acids. However, the protein transducing domain in various embodiments is not limited to the Pep-1 peptide of Seq. No. 3. Skilled artisan in the art would well appreciate techniques for preparing peptides with the same function of Pep-1 peptide by replacing, adding or eliminating a portion of the sequence. Likewise, fusion proteins according to embodiments are produced by replacing, adding or eliminating portions of sequences of biological materials, to include a protein transducing domain Pep-1 containing 15-30 amino acids, hydrophobic domain containing at least 5 tryptophans, hydrophilic domain containing at least 4 lysines, and spacer separating the said two domains and the fusion protein containing the same or like functioning protein transducing domains.

Various aspects of the present invention provide, among other things, fusion proteins of Pep-1-FK506 binding protein, recombinant nucleotides and vectors to produce the said fusion proteins, pharmaceutical compositions and skin external compositions containing the said fusion proteins.

A "fusion protein" refers to a complex of two or more amino acid sequences that are bound to each other. A "fusion protein of Pep-1-FK506 binding protein" refers to a complex containing a FK506 binding protein. A "cell transducing fusion protein" refers to a fusion protein that contains a cell transducing domain, which forms a complex with one or more cargo molecules, e.g., protein moieties or amino acid sequences. A "cell transducing fusion protein of Pep-1-FK506 binding protein" is a complex of a protein transducing domain and a FK506 binding protein as the cargo molecule. In some embodiments, the transduction domain and a cargo molecule (e.g., FK506 binding protein) are fused in a gene level or protein level. In this disclosure the term "fusion protein of Pep-1-FK506 binding protein" is used interchangeably with the same meaning with "Pep-1-FK506BP", "Pep-1-FK506 binding protein", "FK506BP fusion protein", "FK506 binding protein fusion protein", "PEP-FK506BP" or "PEP-FK506 binding protein".

The said "fusion in gene level" means, as well appreciated by skilled artisan in this field, a linear covalent linkage formed from the DNA sequence encoding a certain protein.

And, a "target cell" refers to a cell to which the cargo molecule is to be delivered. For example, the target cells include external cells, i.e., cultured animal cells, human cells or microorganisms.

The term "protein transducing domain" refers to a domain which forms a complex with a peptide or protein, by e.g., a covalent bonding. The protein transducing domain facilitates the fused protein containing the transducing domain to enter into a target cell with or without receptor, carrier or energy. And, an example of such transducing domains can be Pep-1 peptide (Sequence No. 3).

The term "target protein" refers to a molecule which is bonded to a protein transducing domain so as to form a cell transducing fused protein. The term "delivering" protein or peptide refers to "transduction", "penetration", "transporting" and "passing".

In some embodiment, a cell-transducing FK506 binding protein fusion protein contains at least one transducing domain and an FK506 binding protein. In certain embodiments, the transducing domain contains 15-20 amino acids, a hydrophobic domain containing at least 5 tryptophans, a hydrophilic domain containing at least 4 lysines, and a spacer intervening the hydrophobic and hydrophilic domains. At least one amino acid of the protein can be replaced with a functionally equivalent amino acid in the sequence. Amino acid changes in sequences can be selected from the class to which the amino acid belongs to. For example, the hydrophobic amino acid class contains alanine, valine, leucine, isoleucine, phenylalanine, tryptophan, proline and methionine. The polar neutral amino acid class contains glycine, serine, threonine, cysteine, tyrosine, asparagine and glutamine. The positive basic amino acid class contains arginine, lysine and histidine. The negative acidic amino acid class contains aspartic acid and glutamic acid. In some embodiments, the amino acid sequence of the fusion protein in about 85% to about 100% similarity with the particular sequences disclosed herein can be used.

In one embodiment, the FK506 binding protein fusion protein has the amino acid sequence of Seq. No. 7.

In one embodiment, the FK506 binding protein fusion protein contains a protein transducing domain that can be bound at the C- and/or N-terminus of the cargo protein.

Certain embodiments provide a skin care composition containing a cell-transducing FK506 binding protein fusion protein as an active ingredient.

Certain other embodiments provide a pharmaceutical composition containing a cell-transducing FK506 binding protein fusion protein as an active ingredient and a pharmaceutically acceptable carrier.

Some other embodiments provide a recombinant polynucleotide such as sequences present in Seq. No. 6 encoding a cell-transducing fusion protein in which a cDNA of FK506 binding protein is bound to a DNA sequence encoding the protein transducing domain. In some embodiments, the nucleic acid molecule can contain certain variations from Seq. No. 6 due to codon degeneracy Still some other embodiments provide an expression vector for a cell-transducing fusion protein.

EXAMPLES

Various aspects and embodiments of the present invention will be explained in more detail with reference to the following examples.

Preparation

Restriction enzymes and T4 DNA ligase were purchased from Promega (USA), and Pfu polymerase was purchased from stratagene (USA). Tat oligonucleotides were synthesized by Gibco BRL custom primer (USA). IPTG was obtained from Duchefa (Netherland). pET-15b and BL21 (DE3) plasmid was obtained from Novagen (USA), Ni-nitrilo-triacetic acid Sepharose Superflow was purchased from Qiagen (Germany). A cDNA of human FK506 binding protein ("FK506BP") was isolated from human hepatic cDNA library by polymerase chain reaction. All other reagents were extra-pure grade.

Example 1

Construction of Fusion Protein Expression Vectors and Transduction

In the present example, an expression vector for a fusion protein was produced. Human FK506 binding protein was selected as a target protein.

A pET-PEP expression vector containing Pep-1 peptide (KETWWE TWWTEW SQP KKKRKV) (SEQ ID NO: 3) was constructed to produce a fusion protein of Pep-1-FK506 binding protein. Two kinds of oligonucleotide corresponding to Pep-1 peptide (top strand, 5'-TATGAAAGAAACCTG-GTGGGAAACCTGGTGGACCGAATGGTCT CAGC-CGAAAAAAAAACGTAAAGTGC-3' (SEQ ID NO: 1); bottom strand, 5'-TCGAGCACTT TACGTTTTTTTTTCG-GCTGACACCATTCGGTCCACCAGGTTTCCC ACCAG-GTTTCTTTCC-3' (SEQ ID NO: 2)) were ligated into NdeI-XhoI-digested pET-15b vector. Next, we synthesized two primers based on the cDNA sequence of the human FK506 binding protein.

The sense primer, 5'-CTCGAGATGGGAGTGC AGGTG-GAAACCATC-3' (SEQ ID NO: 4) contained a XhoI restriction site, and the antisense primer, 5'-GGATCCTCATTC-CAGTTTTAGAAGCTCCAC-3' (SEQ ID NO: 5) contained a BamHI restriction site.

An expression vector for FK506BP-Pep-1 fusion protein and an expression vector for Pep-1-FK506BP-Pep-1 fusion protein were constructed in the same way.

PCR was performed in a thermal cycler (Perkin-Elmer, model 9600). Reaction mixture in a silicon tube was heated at 94° C. for 5 min.

After PCR, the reaction product was isolated by agarose-gel electrophoresis. Next, the product was ligated into TA-cloning vector (Invitrogen, San diego, USA) and the ligated product was transformed into competent cells. The plasmid was isolated from transformed bacteria by an alkaline lysis method. The cDNA of the human FK506 binding protein was excised from TA vector by XhoI and BamHI restriction enzymes, and inserted into the PEP expression vector. An *E. coli* BL21 (DE3) clone transformed with Pep-1-FK506BP was selected, and the colony was inoculated into 100 ml of LB media and induced for the over-expression of the protein by adding 0.5 mM of IPTG. The over-expressed fusion protein of Pep-1-FK506 binding protein was identified by SDS-polyacrylamide gel electrophoresis and western blot analysis.

Example 2

Expression and Purification of Fusion Proteins

*E. coli* BL21 (DE3) transformed with pPep-1-FK506BP was inoculated and cultured in LB medium containing ampicillin and cultured at 37° C. stirring at 200 rpm. When the bacterial concentration (the optical density at 600 nm) in the cultured medium reached O.D.$_{600}$=0.5-1.0, IPTG was added into the cultured medium with a final concentration of 0.5 mM and 1 mM, and then the cells were cultured for another 12 hrs at 30° C.

The harvested cells in binding buffer (5 mM imidazole, 500 mM NaCl, 20 mM Tris-HCl, pH 7.9) were lysed by sonication. The clarified cell extract was loaded onto a Ni$^{2+}$-nitrilotriacetic acid Sepharose affinity column (Qiagen, USA) under native conditions. After washing with 10 volumes of binding buffer and six volumes of washing buffer (60 mM imidazole, 500 mM NaCl, and 20 mM Tris-HCl, pH 7.9), the fusion proteins were eluted with eluting buffer (1M imidazole, 500 mM NaCl, 20 mM Tris-HCl, pH 7.9.) Fractions containing the fusion protein were combined and salts were removed with a PD-10 column (Amersham, Germany). Protein concentrations were estimated by the Bradford procedure using bovine serum albumin as a standard (Bradford, 1976).

Figure 6:
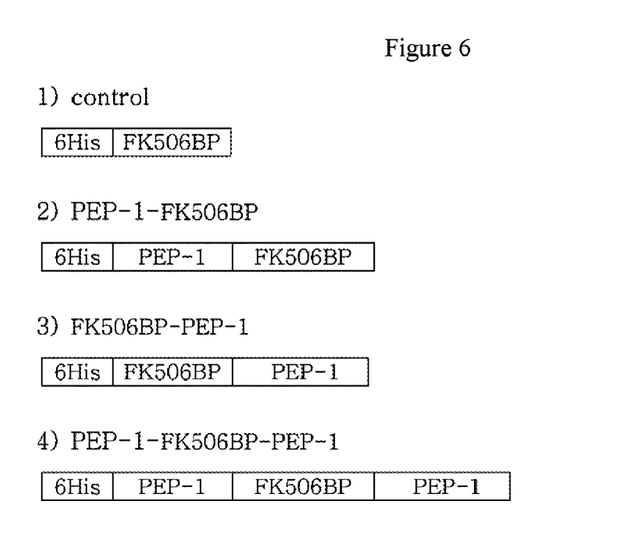
FIG. 6 is schematic diagrams of fusion proteins of FK506 binding protein.

Diagrams of FK506BP-Pep-1 fusion protein in which a Pep-1 peptide is bound to the carboxyl terminal of FK506 binding protein and Pep-1-FK506BP-Pep-1 fusion protein in which a Pep-1 peptide is bound to the amino terminal and another Pep-1 peptide is bound to carboxyl terminal are shown in FIG. 6.

Example 3

Fibroblast Cell Culture and Transduction of Fusion Proteins

The human skin primary fibroblast cells obtained from Catholic University medical school (Korea) were cultured in Dulbecco's modified Eagle's medium (DMEM) containing 20 mM HEPES/NaOH (pH 7.4), 5 mM NaHCO$_3$, 10% fetal bovine serum (FBS) and antibiotics (100 m/ml streptomycin, 100 U/ml penicillin) at 37° C. under a humidified condition of 95% air and 5% CO$_2$. For the transduction of Pep-1-FK506 binding proteins, skin cells were grown about 4-6 hours to confluence on a 6-well plate. The culture medium was then replaced with fresh solution containing 10% fetal bovine serum. After skin cells were treated with one of 3 kinds of fusion protein of the FK506 binding protein (Pep-1 peptide is bound C-, N- or C-/N-terminus of FK506 binding protein respectively) for 1 hr, the cells were then treated with trypsin-EDTA and washed with phosphate-buffered saline (PBS). Thereafter the cells were harvested for the preparation of cell extracts to perform Western blot analysis.

Additionally, cell culture and transduction were performed with HaCaT (Human Keratocyte cell) and B16 cells (Mouse Melanoma cell) obtained from ATCC to identify transducability of the FK506BP fusion proteins.

Example 4

Western Blot Analysis

Western blot analysis was performed to identify intracellular transduction of the fusion protein of FK506 binding protein. The protein was purified in nature form. After incubated with the FK506BP fusion protein (1-12 μM), the skin cells were harvested and subject to the Western Blot analysis.

The transduced Pep-1-FK506BP proteins on the polyacrylamide gel were electrophoretically transferred to a nitrocellulose membrane. The membrane was blocked in Phosphate buffered saline (PBS) solution containing 5% non-fat milk and was then incubated for 1 hr at room temperature with anti-histidine polyclonal antibodies (Santa Cruz Biotechnology; dilution 1:1,000). After washing, the membrane was incubated for 1 hr with mouse anti-rabbit IgG antibodies which are conjugated to horseradish peroxidase and diluted 1:10,000. The membrane was incubated with a chemiluminescent substrate and exposed to Hyperfilm ECL (Amersham Biosciences).

Example 5

Stability of the FK506BP Fusion Protein Transduced into Skin

To identify the intracellular stability of FK506BP fusion, the skin cell was cultured in a 6-well plate. After 4-6 hrs of incubation, the media was replaced with fresh media that did not contain fetal bovine serum. Thereafter, one of 3 kinds of the fusion protein of FK506BP was added to the each sample, respectively. After 1 hr culture, the cells were then treated with trypsin-EDTA and washed with phosphate-buffered saline (PBS). Thereafter the cells were cultured (1-60 hrs) in media containing FBS, and harvested for the preparation of cell extracts to perform the Western blot analysis and the activity analysis.

Example 6

Immunity Inhibition Effect

To test the ability of the fusion protein to inhibit the immunity response caused by lipopolysaccharides, the skin cell was cultured in a 6-well plate, and the media was replaced with fresh media that did not contain fetal bovine serum. Thereafter, one of 3 kinds of the fusion protein of FK506BP was added to the each group of cells, respectively. After lipopolysaccharides were added, the expression of cyclooxygenase-2 was monitored via the Western Blot analysis.

The results were the followings.

1) Over-expression and purification of FK506BP fusion proteins

Figure 1:
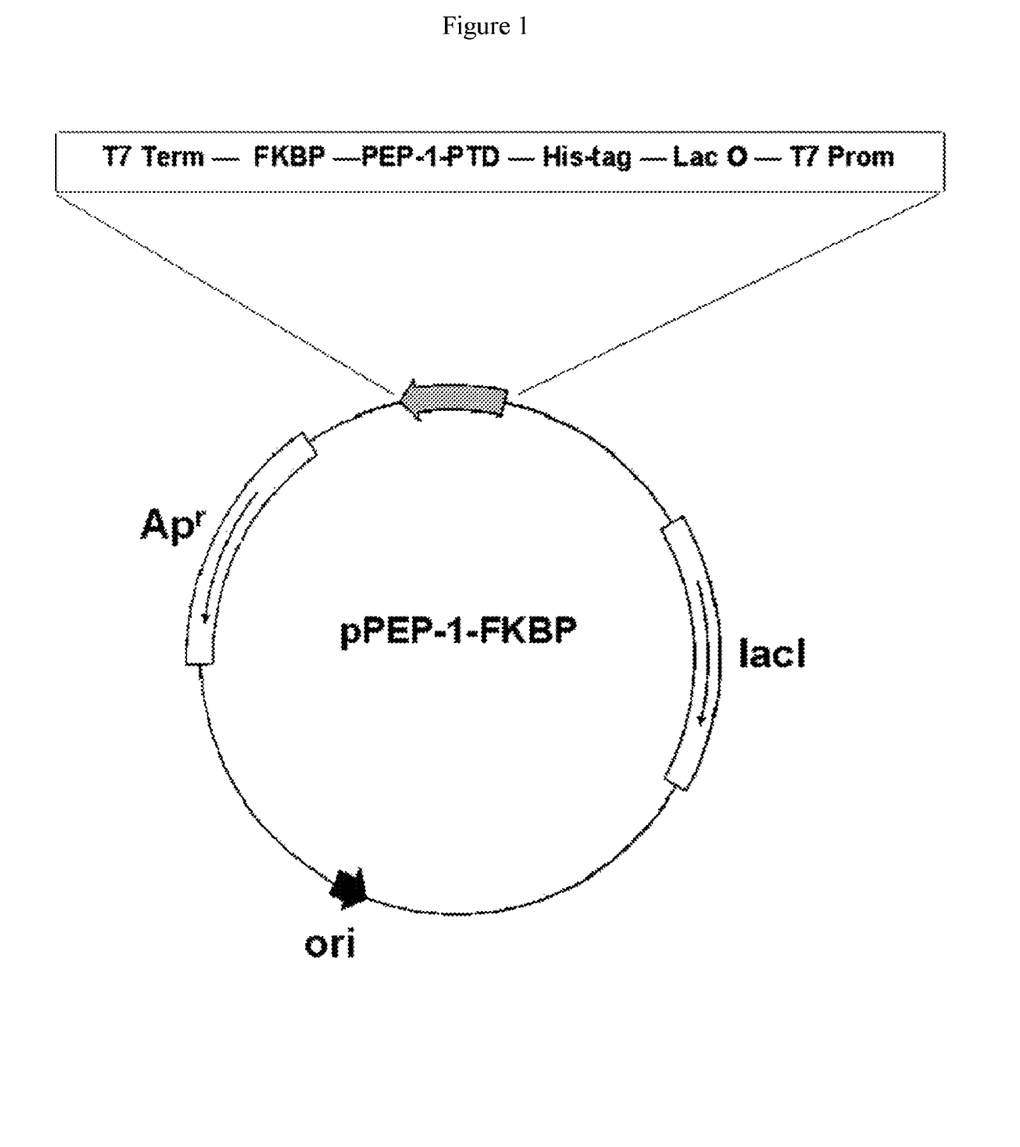
FIG. 1 is a schematic diagram of a vector for a fusion protein of FK506 binding protein. The said vector was produced by modifying a vector pET-15b. A DNA of synthetic Pep-1 oligomer was inserted between Nde 1 and Xho 1 restriction sites, and a cDNA of human FK506 binding protein was inserted between Xho 1 and BamH 1 restriction sites. The expression of the protein was induced by IPTG.

To over-express a fusion protein of FK506BP, a Pep-1-FK506BP expression vector was formed that contains consecutive cDNA sequences encoding the human FK506BP, Pep-1 peptide (21 amino acids) and six histidine residues at the amino terminus (FIG. 1). We also constructed the FK506BP-Pep-1 and Pep-1-FK506BP-Pep-1 expression vectors in the same way.

Figure 2:
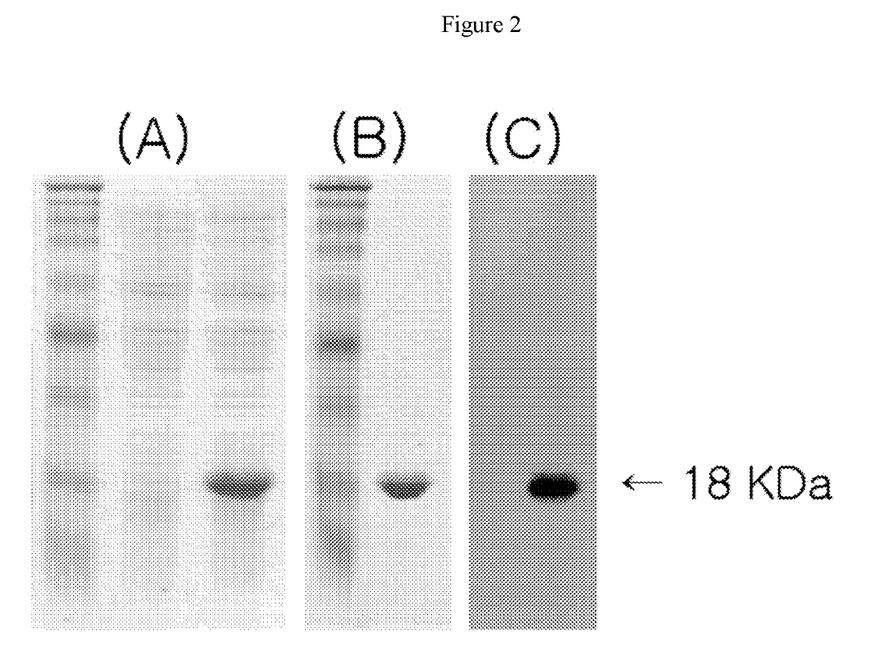
FIG. 2 shows a cellular protein extract and a fusion protein of FK506 binding protein which were purified and isolated by 12% SDS-PAGE(A, B), and then analyzed by western blotting using anti-rabbit polyhistidine antibody(C).

Following the induction of over-expression of the fusion protein by IPTG, the cells were ultrasonicated at 4° C., and centrifuged. And supernatant fractions of the cell extract were separated by 12% SDS-Polyacrylamide gel electrophoresis. FIG. 2 is the result of the SDS-PAGE stained with Coomassie brilliant blue (FIGS. 2A and 2B) and the western blot analysis (FIG. 2C) showing the over-expressed total protein and the purified fusion protein of FK506BP. Lane 2 in FIG. 2A represents over-expressed fusion protein induced by 0.5 mM IPTG treatment compared to the non-treated control.

Since the fusion proteins, Pep-1-FK506BP, FK506BP-Pep-1 and Pep-1-FK506BP-Pep-1 contain 6 consecutive histidine residues in the N- and/or C-terminus, it is possible to purify at least 95% of proteins by the single step process using the immobilized metal-chelate affinity chromatography. FIG. 2B is the result of Coomassie brilliant blue staining of the purified Pep-1-FK506BP fusion protein.

The over-expressed and purified FK506BP fusion protein was identified by the western blot analysis once again. As shown in FIG. 2C, The Western blot analyses using antibodies specifically recognizing histidines or FK506BP visualized a major band of the Pep-1-FK506BP at the same location to the protein as shown in FIG. 2A.

2) Transduction of the FK506BP Fusion Protein into Skin

Figure 3:
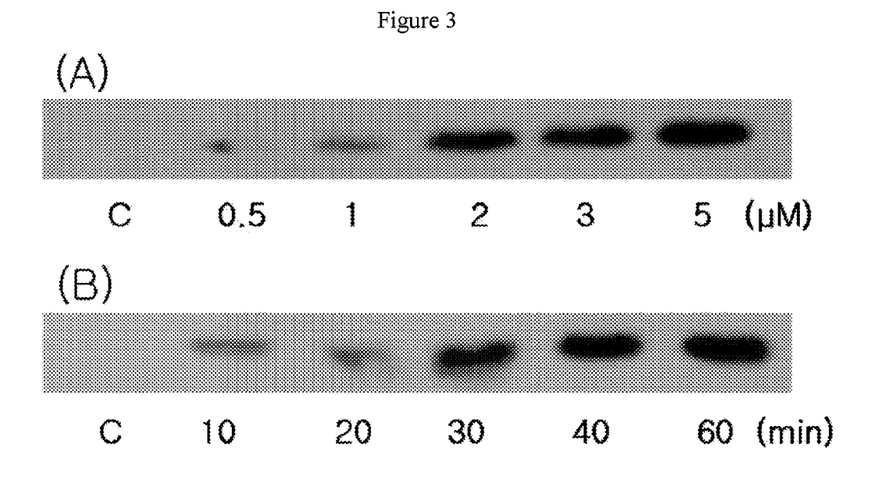
FIG. 3 shows results of western blot analysis of the intracellular transduction efficiency of the fusion protein with various doses (A) and at various times (B).

The transducibility of the purified FK506BP fusion proteins in native form was examined in various concentrations and in various time limits. As shown in FIG. 3, it was identified that the native Pep-1-FK506BP fusion protein was transduced into skin cells in a time- and concentration-dependent manner when monitored via the western blot analysis. FIG. 3A shows the result obtained from cells treated with 0.5-5 µM Pep-1-FK506BP fusion proteins for 60 min. FIG. 3B shows the result obtained from cells treated with 5 µM Pep-1-FK506BP for 10-60 min. Transduction rate of the Pep-1-FK506BP was identified to increase in a concentration-dependent manner. The Pep-1-FK506BP was transduced in 10 min. And, transduction rate of the Pep-1-FK506BP was identified to increase in a time-dependent manner. These results show that Pep-1-FK506BP is transduced in a time- and concentration-dependent manner.

Figure 4:
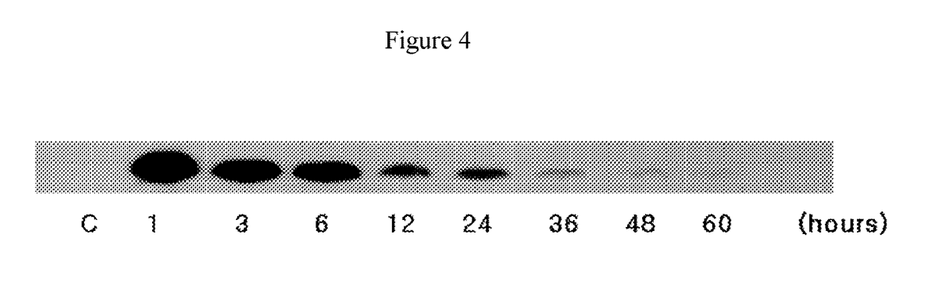
FIG. 4 shows results of western blot analysis of the intracellular transduction efficiency of the fusion protein with 1-60 hr.

FK506BP fusion protein transduced into skin cells should be stable for a long time in order to be used in protein therapy. As shown in FIG. 4, intracellular-transduced Pep-1-FK506BP fusion protein was degraded with time, but at least for 48 hours the fusion protein existed in cells. Therefore, the intracellular-transduced FK506BP fusion protein was stable at least for 48 hrs, the fusion protein is thought to be used in protein therapy.

3) Biological Activity of FK506 Binding Protein Fusion Protein

Figure 5:
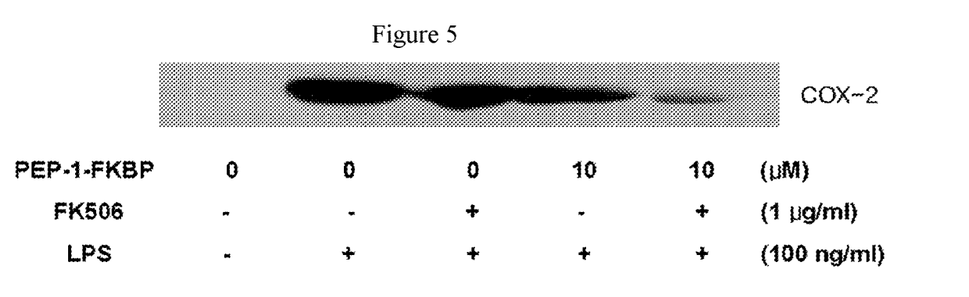
FIG. 5 shows results of western blot analysis of the expression of a lipopolysaccharide-induced cyclooxygenase 2 by a fusion protein of Pep-1-FK506 binding protein. Skin cells were treated with 10 μM of the fusion protein of Pep-1-FK506 binding protein, FK506 binding protein as a control, and adding FK506 or not adding FK506 combination.

FK506BP fusion protein transduced into skin cells should be biologically active in order to be used in the protein therapy. Therefore, it is a very important to confirm if FK506 binding proteins in the fusion protein can be biologically active after transduced into cells. In order to identify the biological activity of the purified FK506BP fusion protein, the expression of cyclooxygenase-2 induced by lipopolysaccharides was tested by the western blot analysis (FIG. 5). It is identified that the purified Pep-1-FK506BP fusion protein inhibited apoptosis and the expression of cyclooxygenase-2 induced by lipopolysaccharides in a time- and concentration-dependent manner. And, the treatment together with FK506, the immune suppressive substance was more effective.

FIGS. 1-5 show the said results 1)-3) of Pep-1-FK506 fusion protein. The fusion protein in which the protein transducing domain is bound to N-terminus of the protein represents about 70-80% efficiency of the Pep-1-FK506 fusion protein in transduction rate and biological activity. And, the Pep-1-FK506-Pep-1 fusion protein in which the protein transducing domains are bound to the N- and C-terminus of the protein shows 1.7-2.2 folds efficiency in transduction rate and biological activity (Data not shown).

Embodiments of the present invention provides an effective transducing method for the human FK506 binding protein as protein level. Since a FK506 binding protein is a major functional protein for treating atopy dermatitis, the fusion protein of the FK506 binding protein can be used in protein therapy.

According to embodiments, the FK506 binding protein is transduced into cells and protects skin cells and tissues. Thus, the fusion protein can be used as functional cosmetics or pharmaceutical compositions.

The sequence listing disclosed herein is of FK506 binding protein in which at least one protein transducing domain is bound to the N- and/or C-terminus of the FK506 binding protein, and the polynucleotides encoding the proteins.

What is claimed is:

1. A recombinant polynucleotide comprising at least one DNA sequence encoding a cell-transducing moiety and a cDNA encoding an FK506 binding protein moiety, wherein the polynucleotide comprises the sequence of SEQ ID NO:6.

2. A recombinant polynucleotide comprising at least one DNA sequence encoding a cell-transducing moiety and a cDNA encoding an FK506 binding protein moiety, wherein the polynucleotide comprises the sequence of SEQ ID NO:8.

3. A recombinant polynucleotide comprising at least one DNA sequence encoding a cell-transducing moiety and a cDNA encoding an FK506 binding protein moiety, wherein the polynucleotide comprises the sequence of SEQ ID NO:10.

* * * * *